United States Patent [19]

Abele

[11] Patent Number: 5,465,732
[45] Date of Patent: Nov. 14, 1995

[54] FLUOROSCOPICALLY VIEWABLE MULTIFILAR CALIBRATED GUIDEWIRE AND METHOD OF MEASURING OCCLUSIONS WITH CALIBRATED GUIDEWIRES

[75] Inventor: John E. Abele, Concord, Mass.

[73] Assignee: Boston Scientific Corporation, Natick, Mass.

[21] Appl. No.: 861,293

[22] Filed: Mar. 31, 1992

[51] Int. Cl.$^6$ ..................................................... A61B 5/00
[52] U.S. Cl. ............................................................ 128/772
[58] Field of Search ................................. 128/657, 772; 604/164, 170, 280, 282

[56] References Cited

U.S. PATENT DOCUMENTS

| | | | |
|---|---|---|---|
| 4,922,924 | 5/1990 | Gambale et al. | 128/772 |
| 4,932,419 | 6/1990 | de Toledo | 128/772 |
| 5,060,660 | 10/1991 | Gambale et al. | 128/772 |
| 5,084,022 | 1/1992 | Claude | 128/772 |
| 5,144,959 | 9/1992 | Gambale et al. | 128/772 |
| 5,174,302 | 12/1992 | Palmer | 128/657 |

Primary Examiner—Max Hindenburg
Attorney, Agent, or Firm—Owen J. Meegan; Frances P. Craig

[57] ABSTRACT

A calibrated guidewire for use in determining the magnitude of arterial occlusions in the body and a method of using the guidewire. The guidewire includes a flexible sleeve having a distal end and a hemispherical tip having a flat inner surface. A multifilar flexible coil is disposed between the distal end of the sleeve and the tip. The coil has a uniform outer diameter and is formed by two sets of different wires, one of which is radiotransparent and the other of which is radiopaque. The spacings between each of the sets is identical and is defined by the widths of each of the sets to provide regularly spaced radiotransparent areas of indicia that are observable as a fluoroscopic image to enable the user measure of the magnitude of an occlusion in a tubular structure in the body. The multifilar construction extends the entire length of the coil between the sleeve and the tip.

13 Claims, 2 Drawing Sheets

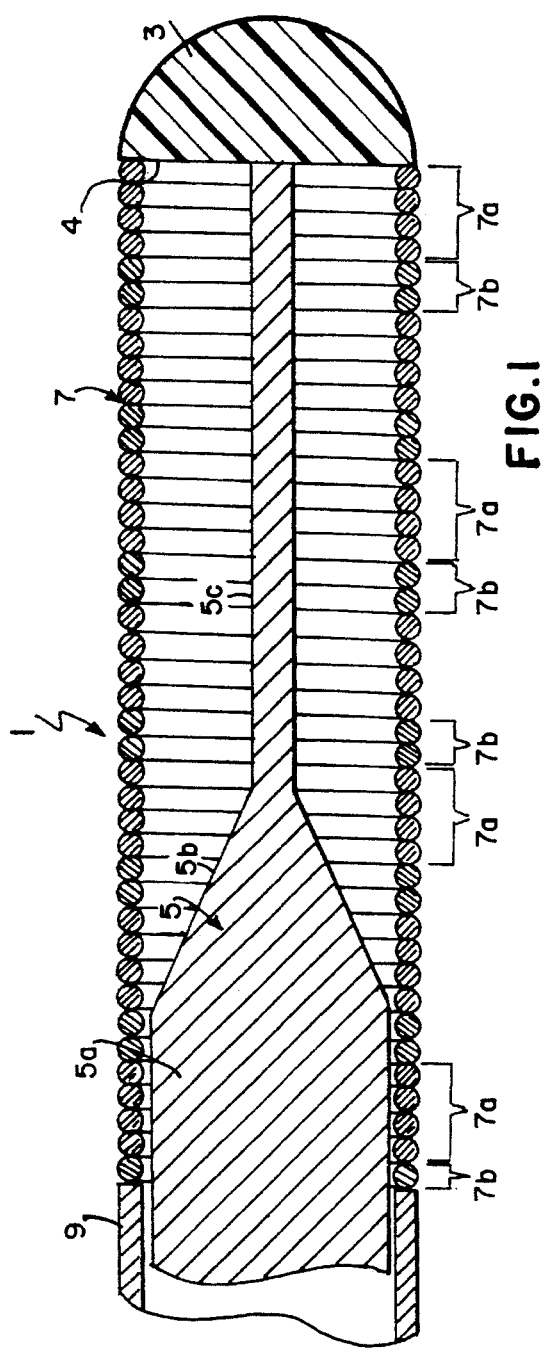
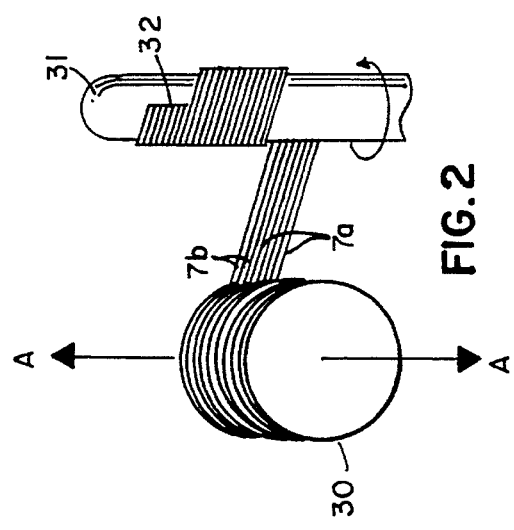

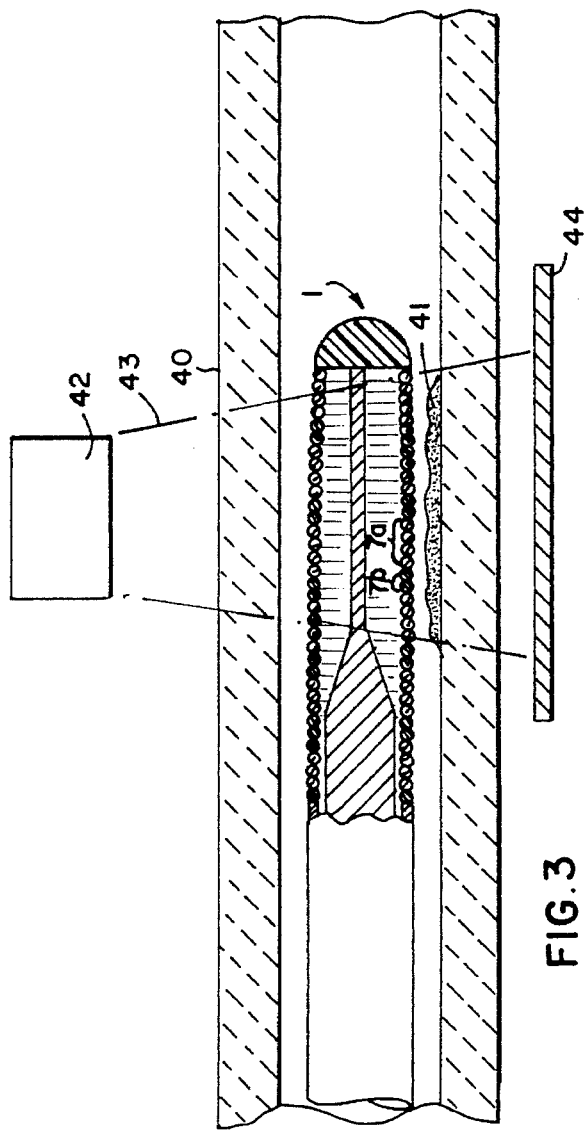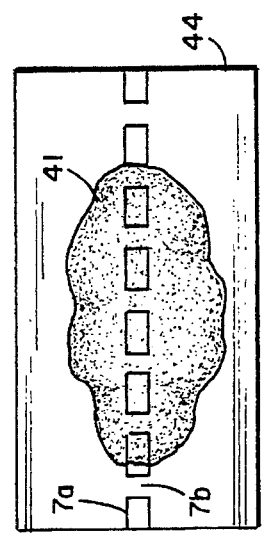

FLUOROSCOPICALLY VIEWABLE MULTIFILAR CALIBRATED GUIDEWIRE AND METHOD OF MEASURING OCCLUSIONS WITH CALIBRATED GUIDEWIRES

FIELD OF THE INVENTION

The present invention relates to an improved guidewire for treating a target tissue site which is accessible by a tortuous path through small vessels and a method of using such guidewires. More specifically, the present invention relates to a guidewire for a catheter which includes a multifilar wound coil at the distal end of the guidewire. The coil serves as a radiological marker to enable a physician to identify the location and magnitude of the target site through radiography. The guidewire can be disposed within a catheter and a core wire can be disposed within the guidewire to stiffen it.

DESCRIPTION OF THE PRIOR ART

Blood vessels and other tubular structures in the body often undergo narrowing and the formation of occlusions. These vessels can be restored to their original diameters by various medical means, especially through the use of balloon catheters. A balloon catheter dilates the vessels by expanding a balloon on the distal end. The balloon tip is inflated by the physician when it is placed within an occlusion of a blood vessel and inflation dilates the vessel to form a clear path therethrough. A flexible guide wire is disposed within the catheter to stiffen it and to provide guidance to the site of the occlusion. Guide wires usually are made of radiopaque material so that their location can be identified during a surgical procedure through radiological viewing.

Use of X-ray imaging to view the guide wire, however, does not always identify the extent of the occlusion. Frequently the length and thickness of the occlusion must be identified so that the physician can utilize the correct balloon size during the surgery.

The prior art has described measuring the length and thickness of an occlusion by incrementally spaced radiopaque marker bands on the outside of the catheter itself. Catheters with marker bands frequently are limited in that they cannot always be positioned directly in the vessel or in a region of the vessel where the occlusion is located. Special catheters for sizing occlusions in vessels have been developed but they require multiple catheter use and exchanging one for another.

Exemplary of markers in the art is the balloon catheter disclosed by LeVeen, U.S. Pat. No. 4,448,195, wherein a radiopaque wire is mitered by machining it at predetermined locations. The miter cuts are used to measure distances on fluoroscopic images since they can be identified on a screen or film. Additionally, the reference teaches banding the outer sleeve of the catheter at both ends of the balloon to indicate the balloon's position to the physician performing the surgery. Mitering the guide wire and banding the sleeve does not provide easily seen views of the size and shape of arterial occlusions. Not only is it difficult to see miter cuts on X-rays but the cuts introduce weak points in the guide wire and makes it more breakable. Banding is less than desirable because the bands increase the diameter of the catheter and make insertion and use more difficult.

Also exemplary of prior art disclosing indicia on a guide wire is the patent to Gambale et al, U.S. Pat. No. 4,922,924. The patent discloses an arrangement where in a proximal section radiopaque and radiotransparent filaments are wrapped on a mandril to form a bifilar coil and in a distal section, only radiopaque filaments are wrapped. The bifilar part of the coil has a moderate radiopacity and the distal end of the coil is completely radiopaque. The moderately radiopaque proximal section will not completely obstruct visualization of arteries onto which radiopaque contrast liquid is injected but gauging of the magnitude of an arterial occlusion is extremely difficult. The United States patent to Fettel et al, U.S. Pat. No. 3,978,863 discloses the use of beads made of radiopaque materials to indicate the location of the tip of the catheter and the expandable balloon at the tip. We have found that the beads add bulk to the catheter and can make the insertion process more difficult.

In a co-pending application of Flight et al, Ser. No. 786,061, filed Oct. 31, 1991 and assigned to the same assignee as the present invention, a disclosure is made of an array of radiopaque markers incrementally disposed within a radiotransparent coil fitted at the end of a catheter. The markers can be seen on an X-ray of the artery being studied to identify the magnitude of an occlusion. The array of markers, however, can be somewhat difficult to assemble on the guidewire thus increasing its cost.

SUMMARY OF THE INVENTION

According to the present invention I have discovered a novel flexible calibrated multifilar coil that can be used both as a calibrating tool and as a guidewire for a catheter and a method of using the calibrated coil. The multifilar coil is disposed at the distal end of the guidewire and can be used to provide viewable reference points on fluoroscopic images thereby to calibrate vessel dimensions similar to placing a ruler against an object to be measured. According to the present invention two sets of wires (or filaments, but herein wires) are wrapped around a mandrel a sufficient number of times to produce a coil of a predetermined length. One of the sets is radiopaque and the other set is radiotransparent. The wires of each set can have a diameter between about 0.07 and 1.2 mm., the diameters of all wires being substantially the same. One set is made up of 4 to 6 wires and the other set is made up of 2 to 4 wires. The wires are tightly wound against each other and form a tightly wound, flexible multifilar coil. The multifilar coil is then attached to the distal end of a guidewire sleeve and is used as the tip of the guidewire. When using wires with the above dimensions a fluoroscopic image is provided so that the physician can easily and accurately measure the dimensions of an occlusion.

In the preferred embodiment 2 to 4 platinum or tantalum wires forming a radiotransparent set are wound with 4 to 6 steel or nitinol (nickel-titanium alloy) wires to form a radiopaque set. Since the diameters of each of the wires of each of the sets are identical, a wrapped coil of these wires on a cylindrical mandrel will produce a coil of uniform outside diameter thereby eliminating bumps or rigid segments within the guidewire that would compromise the performance of the product. In the case of using plastic wires, care has to be taken to insure that the ultimate diameter after wrapping is such the uniform coil diameter is attained. Suitable plastic materials can be, for example, ultra high density polyethylene or polyethylene terephthalate.

The tip of the guidewire can be used as a calibrated gauging tool with the radiotransparent sets appearing as markings on a ruler in the fluoroscopic image when they are placed against an occlusion thereby to enable the physician to accurately gauge its magnitude. Moreover, the guidewire can be used to advance other devices such as an angioplastic balloon catheter or stent device thereby minimizing the need to exchange catheters or guidewires during the surgery.

BRIEF DESCRIPTION OF THE DRAWINGS

FIG. 1 is a side elevational view in cross-section of a guidewire with a multifilar coil disposed at the end of a flexible sleeve.

FIG. 2 is a schematic view of one embodiment of a mechanism to wrap radiopaque and radiotransparent wires for use in the guidewire of the present invention.

FIG. 3 is a schematic view of an X-ray system with a cross-sectional view of the guidewire of the present invention disposed in a blood vessel so as to enable a physician to locate and gauge an occlusion. FIG. 3A is a schematic view of an X-ray image of the guidewire measuring an occlusion.

DESCRIPTION OF A PREFERRED EMBODIMENT

Referring to FIG. 1 of the drawing a core wire 5 is shown with a distal end that is disposed within a gauging section of a guidewire 1. The core wire 5 tapers from a larger body section 5a to a smaller diameter section 5c. The reduction in diameter is provided at the necked down section 5b. The diameter of the body section 5a of the core wire 5 is between about 0.4 and 1.5 mm., preferably about 1 mm. The diameter of the gauging section 5c is between about 0.1 mm. and 0.2 mm. with 0.15 mm. being preferred.

The core wire 5 is disposed within a flexible multifilar coil 7. A hemispherical tip 3 formed of a radiopaque material such as platinum or gold is disposed at the end of the core wire 5. Tip 3 has a flat inner surface 4 which establishes a reference point for the surgeon to measure the magnitude of occlusions as will be described hereinafter.

The coil 7 is attached to the periphery of the inner surface 4 of the tip 3 by welding, brazing or soldering. The proximal end of coil 7 is attached to a plastic sleeve 9, also by welding or with an adhesive. The coil 7 is formed of co-wrapped sets of wires 7a and 7b. Set 7a is formed of a predetermined number of radiopaque wires, each having a diameter between about 0.1 mm. Set 7b is formed of a predetermined number of radiotransparent wires, each having a diameter between about 0.1 mm. In the embodiment shown, set 7a has four wires and set 7b has two wires. The number of wires in each set can be varied as desired and the number of transparent wires can exceed the number of opaque wires. The principal requirement is that the bifilar coil 7 extends from the sleeve 9 to the tip 3 and that all of the wires of each set are tightly wound and abut each other to form a tightly wound, flexible multifilar coil. The important relationship between the two sets of wires 7a and 7b is that the set 7a shows as radiopaque on an X-ray and set 7b shows as radiotransparent on the X-ray. Thus one set, the radiopaque set for example, might have two wires and the radiopaque set might have four wires. Also important is that one set of radiotransparent wires be arranged so as to be sequentially disposed on the set of coils 7 whereby to regularly appear at predetermined intervals. In this way, since the diameters of the individual wires are known, the spacings between radiotransparent and radiopaque wires will appear as a ruler when placed against an occlusion in a vessel so as to enable a surgeon to gauge its length and determine its location.

Referring to FIG. 2 a device to wrap the wires and form the calibrated guidewire as shown. As seen a predetermined array of wires 7a and 7b are pulled from reels 30 that are rotatable on an axis A and also movable elevationally on the same axis. The wires are drawn onto a mandrel 31 that is rotatable around its long axis. In the initial setup the wires 7a and 7b are fitted into a slot 32 formed in the mandrel. The mandrel is then carefully rotated and the wires forming sets 7a and 7b are drawn onto it to form the calibrated guidewire coil. The mandrel 31 is sufficiently long to hold a large number of wrappings of sets. In the embodiment shown the two wires 7b are radiotransparent and the four 7a are radiopaque. When wrapped the wires 7b form radiotransparent bands in an otherwise radiopaque coil.

Several wrappings are made around the mandrel 31 and the coil 7 is then removed. It can be cut to provide a coil of an appropriate length for use with a guidewire, As shown in FIG. 3 the guidewire is disposed in an artery 40. An occlusion 41 is formed in the artery 40 and is disposed beneath the guidewire 1. X-rays which are used to examine the arteries pass through the walls of the artery 40 through the tip of the guidewire 1 and through the occlusion 41. The view of the X-rays will enable the surgeon to identify the length of the occlusion through the ruler-like views which occur because of the regularly disposed bands of radiotransparent coils on the guidewire tip. The guidewire 1 has been inserted into the artery 40 by conventional techniques and the X-ray depiction is also made using conventional methods.

A source 42 of X-rays is disposed adjacent the artery 40 being examined and located approximately where the occlusion 41 is supposed to be. An X-ray beam 43 is focused on the site and the X-rays are received by a receptor 44 that can provide a visual representation of the X-ray image. Radiation can pass through the radiotransparent sets of wires 7a but cannot pass through radiopaque sets 7b. On the receptor 44, as shown in FIG. 3A, the radiotransparent sets 7b show up as transparent lines. These lines are shown overlaid upon the image of the occlusion 41 and can provide the surgeon with the ability to gauge, fairly precisely, the magnitude of the occlusion 41.

It is apparent that modifications and changes can be made within the spirit and scope of the present invention. It is my intention, however, only to be limited by the scope of the appended claims.

As my invention I claim:

1. A guidewire for use in determining the magnitude of arterial occlusions in the body, said guidewire comprising:

a flexible sleeve having a distal end;

a tip for said guidewire;

a hollow multifilar flexible coil, said coil being disposed between the distal end of said sleeve and said tip, said coil having a uniform outer diameter and being formed by two sets of different wires, one of said sets being radiotransparent wires and the other being radiopaque, the spacings between each of the sets being identical and being defined by the widths of each of the sets whereby to provide regularly spaced radiotransparent areas of indicia, both sides of which are observable in a fluoroscopic image to enable the user to measure of the magnitude of an occlusion in a tubular structure in the body, the multifilar construction extending the entire length of said coil between the sleeve and the tip.

2. The guidewire according to claim 1 wherein the diameter of the wires in each set is between about 0.07 and 1.2 mm.

3. The guidewire according to claim 1 wherein there are 2 to 4 wires in the radiopaque set and 4 to 6 wires in the radiotransparent set.

4. The guidewire according to claim 1 wherein the radiopaque wires are platinum, tantalum or tungsten and the radiotransparent wires are steel or nitinol.

5. The guidewire according to claim 1 wherein the wires of the coil abut adjacent wires whereby to form a tight, flexible coil.

6. The guidewire according to claim 1 further including a core wire disposed in said sleeve and extending within said coil to said tip.

7. The guidewire according to claim 6 wherein said tip has a hemispherical exterior shape and a flat inner surface facing the distal end of said coil.

8. A method of providing measurement of the magnitude of intravascular occlusions, said method comprising:

positioning the distal end of a guidewire within a bodily vessel proximate to an occlusion within said vessel, said guidewire including a flexible sleeve having a distal end and a tip for said guidewire, said guidewire further having a multifilar flexible coil disposed between the distal end of said sleeve and said tip, said coil having a uniform outer diameter and being formed by two sets of different wires, one of said sets being radiotransparent wires and the other being radiopaque, the spacings between each of the sets being identical and being defined by the widths of each of the sets whereby to provide regularly spaced radiotransparent areas of indicia which are observable in a fluoroscopic image;

X-raying the vessel and said tip and said occlusion and projecting an image of the X-ray on to a receiver, said image including the regularly spaced radiopaque areas and spaced apart by the radiotransparent areas whereby to enable the user to measure of the magnitude of the intravascular occlusion in a tubular structure in the body, the multifilar construction extending the entire length of said coil between the sleeve and the tip.

9. The method according to claim 8 wherein the diameter of the wires in each set is between about 0.07 and 1.2 mm.

10. The method according to claim 8 wherein there are 2 to 4 wires in the radiopaque set and 6 to 8 wires in the radiotransparent set.

11. The method according to claim 8 wherein the radiopaque wires are platinum and the radiotransparent wires are steel.

12. The method according to claim 8 wherein the wires of the coil abut adjacent wires whereby to form a tight, flexible coil.

13. The method according to claim 8 wherein said tip has a hemispherical exterior shape and a flat inner surface facing the distal end of said coil.

\* \* \* \* \*